United States Patent [19]
Backer et al.

[11] Patent Number: 5,567,693
[45] Date of Patent: Oct. 22, 1996

[54] METHOD FOR INHIBITING ANGIOGENESIS, PROLIFERATION OF ENDOTHELIAL OR TUMOR CELLS AND TUMOR GROWTH

[75] Inventors: Joseph M. Backer, Tenafly, N.J.; Peter Bohlen, Cortland Manor; Phaik-Eng Sum, Pomona, both of N.Y.

[73] Assignee: American Cyanamid Company, Madison, N.J.

[21] Appl. No.: 354,688

[22] Filed: Dec. 13, 1994

[51] Int. Cl.$^6$ .......................... A61K 31/65; A61K 47/00; A61K 9/26
[52] U.S. Cl. .......................... 514/154; 514/768; 424/469; 424/470
[58] Field of Search ..................... 514/764, 152, 514/154; 424/469, 470

[56] References Cited

U.S. PATENT DOCUMENTS

| | | | |
|---|---|---|---|
| 3,226,436 | 12/1965 | Pefis et al. | 552/205 |
| 3,518,306 | 6/1970 | Marfell et al. | 552/205 |
| 5,248,797 | 9/1993 | Sum | 552/205 |
| 5,268,384 | 12/1993 | Galardy | 514/419 |

FOREIGN PATENT DOCUMENTS

| | | | |
|---|---|---|---|
| WO92/12717 | 8/1992 | WIPO | A61K 32/65 |

OTHER PUBLICATIONS

Guerin, C. et al, Selective Endothelial Growth Inhibition by Tetracyclines that Inhibit Collagenase *Biochemical and Biophysical Research Communications*, vol. 188, No. 2, 740–745, 1992.

Bogert, C. van den et al, Arrest of in Vivo Proliferation of Zajdela Tumor Cells by Inhibition of Mitochondrial Protein Synthesis *Cancer Research* 41, 1943.

Teicher, B. A. et al, Antiangiogenic Agents Potentiate Cytotoxic Cancer Therapies against Primary and Metastatic Disease *Cancer Research* 52, 6702–6704.

Monks, A. et al, Feasibility of a High–Flux Anticancer Drug Screen Using a Diverse Panel of Cultured Human Tumor Cell Lines *Journal of the national Cancer Institute*, vol. 83, No. 11, 757–766, Jun., 1991.

Stomayor, E. A. et al, Minocycline in combination with Chemotherapy or radiation therapy in vitro and in vivo *Cancer Chemotherapy and Pharmacology*, 30:377–384, 1992.

Leezenberg, J. A. et al, Posible Cytostatic Action of Tetracyclines in the Treatment of Tumors of the Nasopharynx and Larynx *European Jornal of Clinical Pharmacoloy*, 16, 237–241, 1979.

Tamargo, R. et al, Angiogenesis Inhibition by Minocycline *Cancer Research 51, 672–675, Jan, 1991*.

Kroon, A. M. et al, The Antitumour Action of Doxycycline *Drugs Exptl. Clin. Res.*, X(11), 759–766, 1984.

Bogert, C. Van den et al, Arrest of the Proliferation of Renal and prostate Carcinomas of Human Origin by Inhibition of Mitochondrial Protein Synthesis *Cancer Research* 46, 3283–3289, Jul., 1986.

Pruzandki, W. et al, Inhibition of Enzymatic Activity of Phospholipases $A_2$ by Minocycline and Doxycycline *Biochemical Paharmacology, vol. 44, No. 6, 1165–1170, 1992*.

Golub, L. M. et al, Host modulation with tetracycline and their chemically modified analogues *Periodontology and Restorative Dentistry*, 80–90, 1992.

Golub, L. M. et al, Tetracyclines Inhibit Connective Tissue Breakdown: New Therapeutic Implicaations for an Old Family of Drugs *Critical Reviews in Oral Biology and Medicine*, 2(2):297–322 (1991).

Hlavka, J. et al, The 6–Deoxytetracyclines. III. Electrophilic and Nucleophilic Substitution *J. Am. Chem. Soc., 84, 1420, 1962*.

Zucker, S. et al, Diversity of Melanoma Plasma Membrane Proeinases: Inhibition of Collagenoloytic and Cytolytic Activities by Minocycline, *JNCL* vol. 75, No. 3, Sep. 1985.

Greenwald R. A., et al, Tetracyclines Inhibit Human Synovial Collagenase In Vivo and In Vitro, *The Journal of Rheumatology* 1987: 14:1.

*Primary Examiner*—John W. Rollins
*Attorney, Agent, or Firm*—T. S. Szatkowski

[57] ABSTRACT

The invention relates to a method for inhibiting angiogenesis and proliferation of endothelial cells by administering an inhibitory amount of a 7-(hydrogen or di ($C_1$–$C_4$)alkylamino)-8-halogen-9-(substituted)-6-demethyl-6-deoxytetracycline of Formula I:

wherein R, X and W are as defined in the specification. The invention also relates to a method for inhibiting proliferation of tumor cells and tumor growth by administering an inhibitory amount of a compound of Formula I in combination with a chemotherapeutic agent or radiation therapy. The invention also relates to compositions containing an effective inhibitory amount of a compound of Formula I in a pharmaceutically acceptable carrier.

6 Claims, 2 Drawing Sheets

5,567,693

METHOD FOR INHIBITING ANGIOGENESIS, PROLIFERATION OF ENDOTHELIAL OR TUMOR CELLS AND TUMOR GROWTH

BACKGROUND OF THE INVENTION

1. Field of the Invention

The invention relates to a method for inhibiting angiogenesis and proliferation of endothelial cells by administering an inhibitory amount of a 7-(hydrogen or di($C_1$–$C_4$)alkylamino)-8-halogen-9-(substituted)-6-demethyl- 6-deoxytetracycline. The invention also relates to a method for inhibiting proliferation of tumor cells and tumor growth by administering an inhibitory amount of a 7-(hydrogen or di($C_1$–$C_4$)alkylamino)-8-halogen-9-(substituted)-6-demethyl-6-deoxytetracycline in combination with a chemotherapeutic agent or radiation therapy. The invention also relates to compositions containing an effective inhibitory amount of a 7-(hydrogen or di($C_1$–$C_4$)alkylamino)-8-halogen-9-(substituted)-6-demethyl-6-deoxytetracycline in a pharmaceutically acceptable carrier.

2. Description of the Prior Art

In WO92/12717, Brem et al teach that some tetracyclines, particularly Minocycline, Chlortetracycline, Demeclocycline and Lymecycline are useful as inhibitors of angiogenesis. In *Cancer Research* 51, 672–675, Jan. 15, 1991, Brem et al teach that Minocycline inhibits angiogenesis to an extent comparable to that of the combination therapy of heparin and cortisone. In *Cancer Research* 52, 6702–6704, Dec, 1, 1992, Teicher et al teach that tumor growth is decreased and the number of metastases is reduced when the anti-angiogenic agent Minocycline is used in conjunction with cancer chemotherapy or radiation therapy.

It has now been found that certain 7-(hydrogen or di($C_1$–$C_4$)alkylamino)-8-halogen- 9-(substituted)-6-demethyl-6-deoxytetracyclines are unexpectedly better inhibitors of endothelial and tumor cell proliferation than the tetracyclines, especially Minocycline, described by Brem et al and Teicher et al.

SUMMARY OF THE INVENTION

The invention provides a method for inhibiting angiogenesis and endothelial cell proliferation which comprises administering an effective inhibitory amount of a compound of formula I:

Formula I wherein:

R is hydrogen or a di($C_1$–$C_4$)alkylamino;

X is halogen selected from bromine, chlorine, fluorine and iodine;

W is hydrogen or a moiety of the formula:

wherein:

$R_1$ and $R_2$ are hydrogen or ($C_1$–$C_3$)alkyl; B is ($R_3$)$_2$N—; $R_3$NH— or ($C_2$–$C_5$)azacycloalkane wherein $R_3$ is ($C_1$–$C_7$)alkyl or ($C_3$–$C_5$)cycloalkylmethyl; or a pharmaceutically acceptable salt thereof; alone or in combination with a therapeutic agent used in the treatment of an angiogenic disorder; to a warm blooded animal having a disorder characterized by the undesired proliferation of endothelial cells.

The invention also provides a method for inhibiting tumor cell proliferation and tumor growth which comprises administering an effective inhibitory amount of a compound of formula I:

Formula I wherein:

R is hydrogen or a di($C_1$–$C_4$)alkylamino;

X is halogen selected from bromine, chlorine, fluorine and iodine;

W is hydrogen or a moiety of the formula:

wherein:

$R_1$ and $R_2$ are hydrogen or ($C_1$–$C_3$)alkyl;

B is ($R_3$)$_2$N—; $R_3$NH— or ($C_2$–$C_5$)azacycloalkane wherein $R_3$ is ($C_1$–$C_7$)alkyl, or ($C_3$–$C_5$)cycloalkylmethyl; or a pharmaceutically acceptable salt thereof;

in combination with a chemotherapeutic agent or radiation therapy; to a warm blooded animal having a disorder characterized by the undesired proliferation of tumor cells.

The invention also provides a composition for inhibiting angiogenesis and endothelial cell proliferation which composition comprises an amount effective for inhibiting endothelial cell proliferation of a compound of formula I:

Formula I wherein:

R is hydrogen or a di($C_1$–$C_4$)alkylamino;

X is halogen selected from bromine, chlorine, fluorine and iodine;

W is hydrogen or a moiety of the formula:

wherein:

$R_1$ and $R_2$ are hydrogen or $(C_1-C_3)$alkyl;

B is $(R_3)_2N-$; $R_3NH-$ or $(C_2-C_5)$azacycloalkane wherein $R_3$ is $(C_1-C_7)$alkyl, or $(C_3-C_5)$cycloalkylmethyl; or a pharmaceutically acceptable salt thereof;

in a pharmaceutical carrier for administration to a warm blooded animal having a disorder characterized by undesired proliferation of endothelial cells.

The invention also provides a composition for inhibiting tumor cell proliferation and tumor growth which composition comprises an amount effective for inhibiting tumor cell proliferation of a compound of formula I:

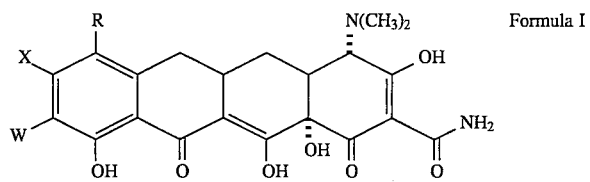

wherein:

R is hydrogen or a di$(C_1-C_4)$alkylamino;

X is halogen selected from bromine, chlorine, fluorine and iodine;

W is hydrogen or a moiety of the formula:

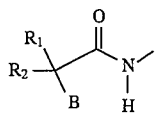

wherein:

$R_1$ and $R_2$ are hydrogen or $(C_1-C_3)$alkyl;

B is $(R_3)_2N-$; $R_3NH-$ or $(C_2-C_5)$azacycloalkane wherein $R_3$ is $(C_1-C_7)$alkyl, or $(C_3-C_5)$cycloalkylmethyl; or a pharmaceutically acceptable salt thereof;

in a pharmaceutical carrier for administration to a warm blooded animal having a disorder characterized by the undesired proliferation of tumor cells.

DESCRIPTION OF THE PREFERRED EMBODIMENT

Figure 1:
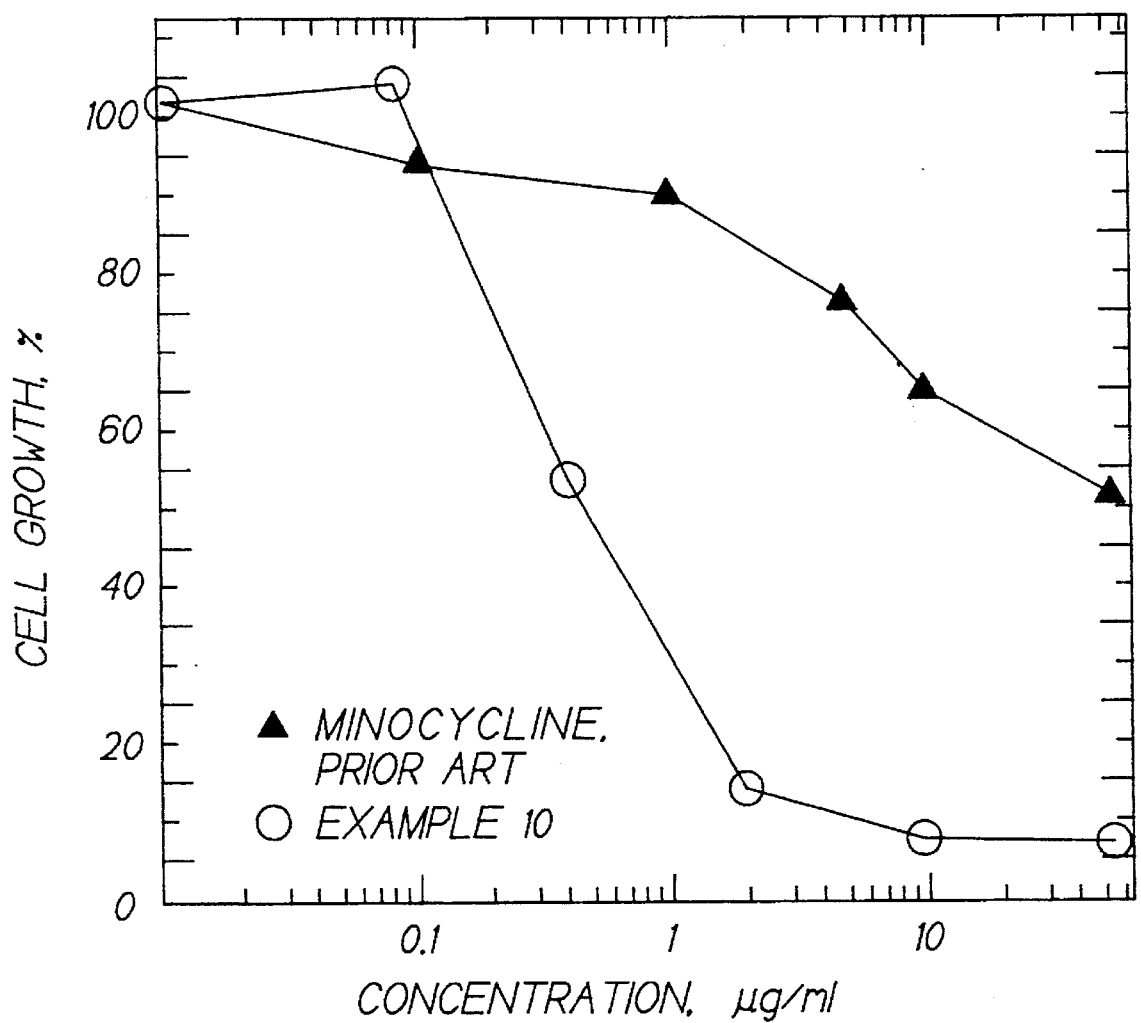
FIG. 1 depicts the effects of the compound of Example 10 on the proliferation of Adult Bovine Aortic Endothelial cells (ABAE) compared to the prior art compound, Minocycline.

Angiogenesis, a biological process that includes the proliferation and migration of endothelial cells, is defined as the growth of new blood vessels, in particular, capillaries and is an essential part of both normal and pathological tissue growth. Characteristic elements of angiogenesis include endothelial cell proliferation, endothelial cell migration, invasion of endothelial cells into tissue, tube formation, and maturation of endothelial cells. Angiogenesis plays a critical role in such beneficial functions as embryogenesis, wound healing and the female reproductive cycle, as well as in such abnormal functions as psoriasis, diabetic retinopathy, rheumatoid arthritis, hemangiomas, and solid tumor formation.

It has now been found that administration of an effective amount of a compound of Formula I inhibits endothelial cell proliferation and tube formation, having the effect of preventing new capillary blood vessels from forming and thus inhibiting angiogenesis. In particular, the compounds of Formula I are cytostatic for endothelial cells, i.e., they inhibit the ability of the cells to divide without affecting other vital cell functions. According to the present invention, angiogenesis is inhibited by the administration of an effective amount of a compound of Formula I. In this regard, the effective amount of a compound of Formula I for inhibiting angiogenesis and endothelial cell proliferation is from about 0.10 mg/kg to about 30.0 mg/kg of body weight, with from about 1.0 mg/kg to about 10.0 mg/kg of body weight being preferred.

The ingrowth of capillaries and ancillary blood vessels is essential for growth of solid tumors and is thus an unwanted physiological response which facilitates the spread of malignant tissue and metastases. Inhibition of angiogenesis and the resultant growth of capillaries and blood vessels is therefore a component of effective treatment of malignancy.

The compounds of Formula I may be administered alone or in combination with another therapeutic agent used in the treatment of an angiogenic disorder. Such therapeutic genistein, suramin, pentosan polysulfate, thalidomide and 2-methoxyestradiol.

The fact that administration of a compound of Formula I inhibits angiogenesis and endothelial cell proliferation to a remarkable degree is quite beneficial for controlling the growth of solid tumors because most if not all solid tumors, like normal tissue, require a steady and sufficient blood supply for optimal growth. Tumors are known to make use of angiogenic growth factors that are produced by the tumor cells in order to attract new blood vessels and ascertain supply with sufficient amounts of nutrients to sustain their growth. Many tumors are well vascularized and the inhibition of the formation of an adequate blood supply to the tumor by inhibition of tumor vascularization, as a result of endothelial cell growth inhibition, is beneficial in tumor growth control. Without a strong blood supply, rapid and prolonged growth of tumor tissue cannot be sustained.

It has also been found that the compounds of Formula I are cytostatic for tumor cell proliferation. The fact that both tumor and endothelial cells are growth inhibited by administration of a compound of Formula I is desirable and advantageous. From a mechanistic point of view, the effect of a compound of Formula I on tumor growth is a dual one, by acting on tumor cell inhibition directly and by reduction of the blood supply indirectly. Both aspects contribute to inhibition of tumor growth and a compound that combines these aspects is extremely advantageous over other drugs which act on only one of the targets.

The administration of a compound of Formula I is effective in controlling the growth of solid tumors. Examples of solid tumors include but are not limited to colon tumors, ovarian tumors, breast tumors, lung tumors, pancreatic, osteosarcoma, prostate and melanoma tumors.

According to the present invention, tumor growth is inhibited by administering an effective amount of a compound of Formula I to a patient having a disorder characterized by the undesired proliferation of solid tumor cells. In this regard, the effective amount of a compound of Formula I for inhibiting tumor cell proliferation and tumor growth is from about 0.10 mg/kg to about 30.0 mg/kg of body weight, with from about 1.0 mg/kg to about 10.0 mg/kg of body weight being preferred.

The compounds of Formula I may be administered alone or in conjunction with a standard tumor therapy, such as chemotherapy or radiation therapy. It is preferred that the compounds of Formula I be administered in combination with a standard therapy: chemotherapy or radiation therapy. While not wishing to be bound by any theory, it appears that the clear effect of the administration of a compound of Formula I to inhibit tumor growth is related to the ability of the compound to inhibit endothelial cell proliferation and hence new blood vessel formation. Such reduction of vascular supply works best when a tumor is significantly reduced in mass after standard chemotherapy or radiation therapy. It is significant that the compound of Formula I can be administered in conjunction with the standard antitumor therapy and, in addition, can be administered on a continuing basis after the standard antitumor therapy. In this way the tumor will grow back slower while the patient is recovering from the side effects of the standard therapy. Chemotherapy or radiation therapy can then be repeated along with the continuation of the administration of compound of Formula I. The effect of this continuation of combination therapy is that the compound of Formula I will be effective in slowing down vascular supply to an already weakened tumor until it is essentially eradicated.

It is also contemplated that administration of a compound of Formula I controls metastases. Metastases also require a blood supply in order to become full blown secondary tumors. Since some metastases are small, administration of a compound of Formula I directly counteracts the angiogenic signal of metastases. Such a compound also contributes to slower metastasis growth because it has a direct effect on tumor cell proliferation.

The compound of Formula I may be administered orally, parenterally, topically, intravenously, or systemically. In addition, for inhibiting tumor cell proliferation and tumor growth, the compound of Formula I may be administered locally directly to the tumor or as a part of a deposited slow release formulation. Administration may be on a daily basis for as long as needed to inhibit angiogenesis, endothelial cell proliferation, tumor cell proliferation or tumor growth. Alternatively, a slow release formulation may continue for as long as needed to control tumor growth. This dosage regimen may be adjusted to provide the optimum therapeutic response. For example, several divided doses may be administered daily or the dose may be proportionally reduced as indicated by the exigencies of the therapeutic situation.

In this regard, the compositions of this invention that are useful as inhibitors of angiogenesis, endothelial cell proliferation, tumor cell proliferation and tumor growth contain a pharmaceutically acceptable carrier and an amount of a compound of Formula I, 7-(hydrogen or di($C_1$–$C_4$)alkylamino)-8-halogen- 9-(substituted)-6-demethyl-6-deoxytetracycline or a pharmaceutically acceptable salt thereof, effective to inhibit tumor or endothelial cell proliferation.

The pharmaceutically acceptable salts of the 7-(hydrogen or di($C_1$–$C_4$)alkylamino)-8-halogen- 9-(substituted)-6-demethyl-6-deoxytetracyclines include inorganic salts such as hydrochloride, hydrobromide, hydroiodide, phosphate, nitrate or sulfate; or organic salts such as acetate, benzoate, citrate, cysteine or other amino acids, fumarate, glycolate, maleate, succinate, tartrate, alkylsulfonate or arylsulfonate. It is contemplated that the 7- (hydrogen or di ($C_1$–$C_4$)alkylamino)- 8-halogen-9-(substituted)-6-demethyl-6-deoxytetracyclines may also be utilized as metal complexes, for example, aluminum, calcium and iron; or as the corresponding Mannich base adducts using methods known to those skilled in the art (Richard C. Larock, Comprehensive Organic Transformations, VCH Publishers, 411–415, 1989). It is known to one skilled in the art that an appropriate salt form is chosen based on physical and chemical stability, flowability, hygroscopicity and solubility. It is also known to those skilled in the art, that the above salts are made from the corresponding acid, so that hydrochloric acid gives the hydrochloride salt, sulfuric acid gives the sulfate salt, and acetic acid gives the acetate salt.

Depending on the stoichiometry of the above acids used, the salt formation occurs at the C(4)-ring position which has a dimethylamino group (1 equivalent of acid); or with both the C(4)-ring position which has a dimethylamino group and the W group (2 equivalents of acid). The salts are preferred for oral and parenteral administration.

Pharmaceutical compositions are prepared using the compounds of formula I as the active agent for inhibition of tumor and/or endothelial cell proliferation based on the specific application. Any of the compositions may also include preservatives, antioxidants, immunosuppressants, and other biologically and pharmaceutically effective agents which do not exert a detrimental effect on the 7-(hydrogen or di($C_1$–$C_4$)alkylamino)- 8-halogen-9-(substituted)-6-demethyl-6-deoxytetracycline or the cells. For treatment of tumor cells, the composition may include an anti-cancer agent which selectively kills the faster replicating tumor cells, many of which are known and clinically in use. Exemplary anti-cancer agents include melphalan, cyclophosphamide, methotrexate, adriamycin and bleomycin [Sotomayor et al, Cancer Chemother. Pharmacol., (1992), 30:377–384]. It is also contemplated that the compounds of Formula I can be used to treat other angiogenic diseases, in conjunction with appropriate established therapeutic agents for example the anti-cancer agents listed above or anti-inflammatory agents, steroidal or nonsteroidal, such as the corticosteroids or endomethacins. For example, a compound of Formula I maybe used in combination with methotrexate or an anti-inflammatory agent to treat rheumatoid arthritis.

For topical application, the 7-(hydrogen or di($C_1$–$C_4$)alkylamino)-8-halogen-9-(substituted)- 6-demethyl- 6-deoxytetracycline is combined with a carrier so that an effective dosage is delivered, based on the desired activity, at the site of application. The topical composition can be applied to the skin for treatment of diseases such as psoriasis. The carrier may be in the form ointment, cream, gel paste, foam, aerosol, suppository, pad or gelled stick. A topical composition for treatment of eye disorders, such as diabetic retinopathy, consists of an effective amount of a compound of formula I in an ophthalmically acceptable excipient such as buffered saline, mineral oil, vegetable oils such as corn or arachis oil, petroleum jelly, Miglyl 182, alcohol solution or liposome or liposome-like product.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such benzyl alcohol or methyl parabens; antioxidants such as ascorbic acid or sodium bisulfite; chelating agents such as ethylene-diaminetetraacetic acid; buffers such as acetates, citrates, or phosphates and agents for the adjustment of tonicity such as sodium chloride or dextrose. The parental preparation can be enclosed in ampoules, disposable syringes or multiple dose vials made of glass of plastic.

Compositions for oral or systemic administration will generally include an inert diluent in addition to the compound of Formula I. Such compositions may be in the form of tablets or capsules, which can contain any of the following ingredients, or compounds of a similar nature: a binder such as microcrystalline cellulose, gum tragacanth or gelatin; an excipient such as a starch or lactose, a disintegrating agent such as alginic acid, Primogel or corn starch; a lubricant such as magnesium stearate; or a glidant such as colloidal silicon dioxide. In addition, the tablet or capsule may contain various other materials which modify its physical form, for example, coating of sugar, shellac, or other enteric agents. When a capsule is employed, it can contain in addition to material of the above type, a liquid carrier such as a fatty oil.

The compounds of formula I may also be embedded in a biocompatible controlled release matrix delivery device and inserted at the tumor site to maintain therapeutically effective levels of the compound in the target tumor. The device may be in the form of a rod, pellet, disc, microspheres, tablet or other shape and may be prepared by any of a number of methods including molding, compression, coacervation or extrusion. The device is designed to produce predictable and reproducible drug release rates. This may be a continuous zero-order profile or the formulation can be varied to give a programmed release profile which may have an initial burst, pulsatile release or another pattern which may conform to chronobiological or other therapeutic requirements. The matrix preferably contains a biodegradable polymer which may include polylactides, polyglycolide, polyanhydride, and copolymers of these substances. Nonbiodegradable polymers may also be used such as silicones or certain acrylic resins.

The compounds according to Formula I which are used for the novel method and composition of this invention may be readily prepared in accordance with the following schemes.

A method for producing a 7-(hydrogen or di ($C_1$–$C_4$)alkylamino)-8-halogen-9-(substituted)-6-demethyl-6-deoxytetracyclines or its mineral acid salt, 3, is shown in Scheme I. The substitution at the 9-position, in this invention, is either 9-hydrogen or 9-[(substituted glycyl) amido]. Scheme 1 illustrates the method for making a 7-(hydrogen or di ($C_1$–$C_4$) alkylamino)-8-halogen-9[(substituted glycyl)amido]-6-demethyl-6-deoxytetracycline.

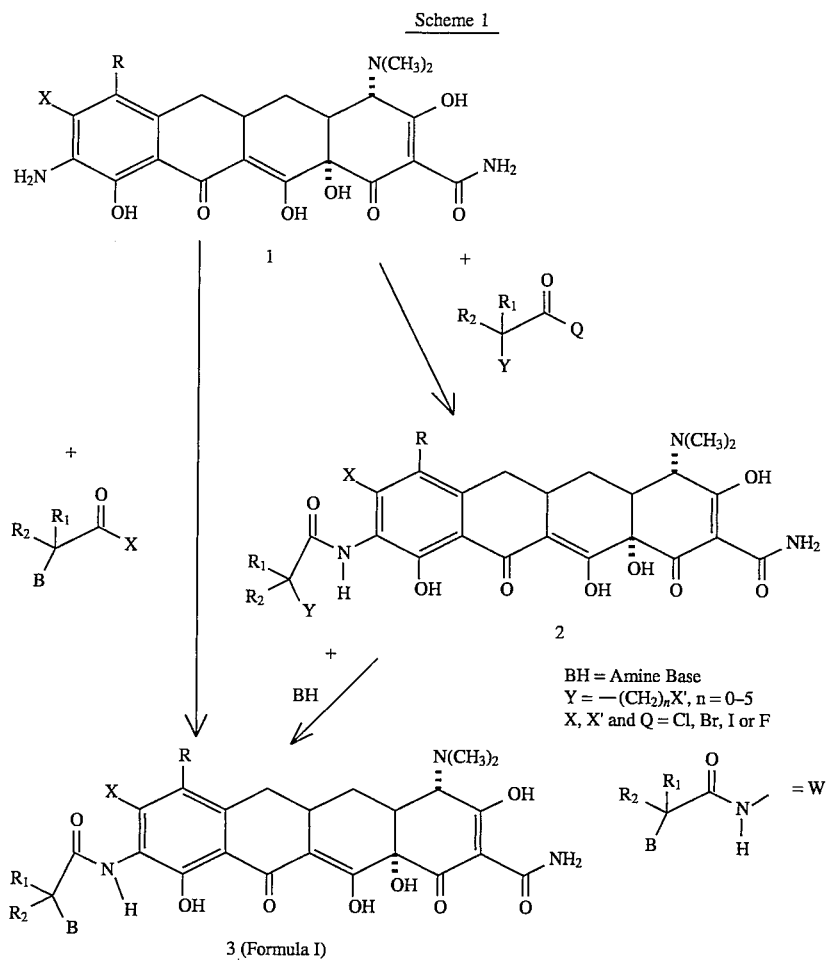

Scheme 1

In accordance with Scheme 1, a 9-amino-7-(hydrogen or di($C_1$–$C_4$)alklyamino)-8-halogen-6-demethyl- 6-deoxytetracycline, 1, or the mineral acid salt or halide salt, prepared by the procedure in U.S. patent applications, Ser. No. 928,578, filed Aug. 13, 1992 now U.S. Pat. No. 5,420,252, and Ser. No. 214,992, filed Mar. 21, 1994 now U.S. Pat. No. 5,430,162, is treated at room temperature for from 0.5 to 2.0 hours with an acid chloride of the formula:

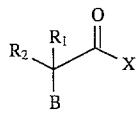

wherein $R_1$, $R_2$, and B are defined hereinabove and X is bromine, chlorine, iodine or fluorine; in the presence of a suitable acid scavenger, in a suitable solvent, to form the corresponding 7-(hydrogen or di($C_1$–$C_4$)alkyl-amino)-8-halogen-9-(substituted)-6-demethyl-6-deoxytetracycline, 3, or the mineral acid or halide salt.

A suitable acid scavenger is selected from sodium bicarbonate, sodium acetate, pyridine, triethylamine, N,O-bis(trimethylsilyl)acetamide, N,O-bis(trimethylsilyl)tri-fluroroacetamide, potassium carbonate, a basic ion exchange resin and equivalent thereof. A suitable solvent is selected from water, tetrahydrofuran, N-methylpyrrolidone, 1,3-dimethyl-2-imidazolidinone, hexamethylphosphoramide, 1,3-dimethyl- 3,4,5,6-tetrahydro-2(1H)pyrimidinone, 1,2-dimethyoxy-ethane and equivalent thereof.

Alternatively, in accordance with Scheme 1, a 9-amino-7-(hydrogen or di($C_1$–$C_4$)alklyamino)-8-halogen- 6-demethyl-6-deoxytetracycline, 1, or the mineral acid salt or halide salt, is treated with a α-haloacyl halide of the formula:

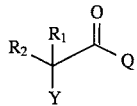

wherein $R_1$ and $R_2$ are as defined hereinabove; Y is —$(CH_2)_n$X', n=0–5 and X' is halogen selected from bromine, chlorine, iodine and fluorine; and Q is halogen selected from bromine, chlorine, iodine and fluorine such as bromoacetyl bromide, chloroacetyl chloride, 2-bromopropionyl bromide or equivalent thereof; in the presence of a suitable acid scavenger, in a suitable solvent, to form the corresponding 9-[(haloacyl)amido]-7-(hydrogen or di($C_1$–$C_4$)alklyamino)-8-halogen-6-demethyl-6-deoxytetracycline, 2, or the mineral acid or halide salt.

The halogen, Y, and the halide, Q, in the haloacyl halide can be the same or different halogens and are selected from bromine, chlorine iodine and fluorine.

The 9-[(haloacyl)amido]-7-(hydrogen or di($C_1$–$C_4$)alklyamino)-8-halogen-6-demethyl-6-deoxytetracycline, 2, or the mineral acid or halide salt, is treated, under an inert atmosphere of nitrogen, argon or helium, with nucleophiles of the formula BH, where B is as defined hereinabove, such as amines or substituted amines or equivalent thereof, in a suitable solvent to form the corresponding 7-(hydrogen or di($C_1$–$C_4$)alkylamino)- 8-halogen-9-[(substituted glycyl)amido]-6-demethyl-6-deoxytetracycline, 3 (Formula I) , or the mineral acid or halide salt.

In accordance with Scheme 2, which illustrates the method of making the 7-(hydrogen or di($C_1$–$C_4$)alkylamino)- 8-halogen-9-(hydrogen)-6-demethyl-6-deoxytetracyclines, 9-amino-8-chloro-4,7-bis(dimethylamino) - 6-demethyl-6-deoxytetracycline, 1, or its mineral acid or halide salt, is converted to a diazonium salt, 4, using procedures known to those skilled in the art including those described in J. J. Hlavka et al, *J. Am. Chem. Soc.*, 84, 1420 (1962).

The diazonium salt, 4, is reduced to 8-chloro- 4,7-bis(dimethylamino)-6-demethyl-6-deoxytetracycline, 3 (Formula I), by heating with alcohol.

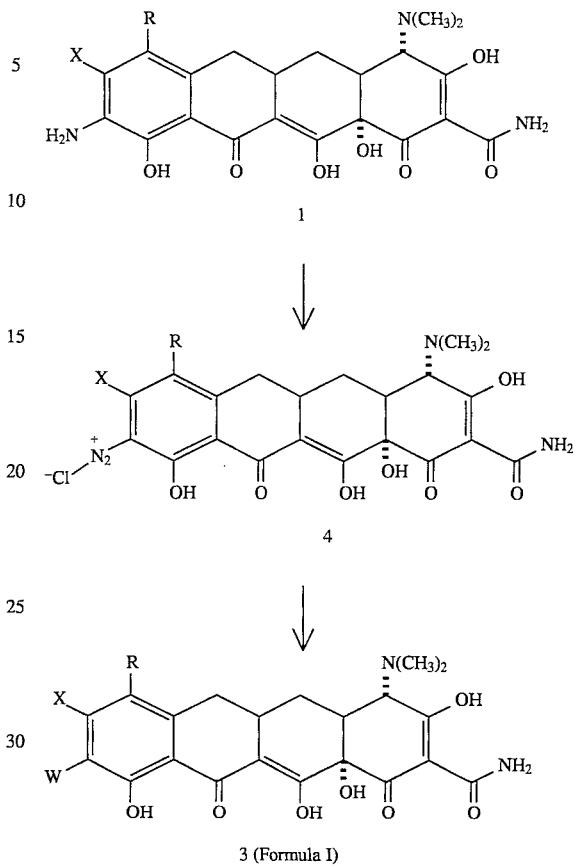

W = Hydrogen

Some of the compounds according to formula I, in the hereinbefore described Scheme I, have centers of asymmetry at the carbon bearing the B substituent. The compounds may, therefore, exist in at least two (2) stereoisomeric forms. The present invention encompasses the racemic mixture of stereoisomers as well as all stereisomers of the compounds whether free from other stereoisomers or admixed with stereoisomers in any proportion of enentiomers. The absolute configuration of any compound may be determined by conventional X-ray crystallography.

The stereochemistry centers on the tetracycline unit (i.e., C-4, C-4a, C-5a, C-12a) remain intact throughout the reaction sequence.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

9-Amino-8-chloro-4-(dimethylamino)-1,4,4a,5,5a,6,11,12 a-octahydro-3,10,12,12a-tetrahydroxy-1,11-dioxo-2-naphthacenecarboxamide hydrochloride To 10 ml of concentrated hydrochloric acid at 0° C. is added 0.20 g of 9-azido-6-demethyl-6-deoxytetracycline, prepared by the procedure described in *J. Am. Chem. Soc.*, 84: 1426–1430. The reaction is stirred at 0° C. for 1.5 hours and concentrated in vacuo to give 0.195 g of the desired product.

MS(FAB): m/z 464(M+H).

EXAMPLE 2

[4S-(4α, 12aα)]-9-[(Bromoacetyl)amino]-8-chloro-4-dimethylamino)-1,4,4a,5,5a,6,11,12a-octahydro-3,10,12,12 a-tetrahydroxy-1,11-dioxo-2-naphthacenecarboxamide hydrobromide (2-A)

A 25° C. solution of 1.25 G of product from Example 1 (1 equivalent), 12 ml of 1,3 -dimethyl-3,4,5,6 -tetrahydro-2 (1H) -pyrimidinone, hereinafter called DMPU, and 6 ml of acetonitrile is treated with 0.56 G of bromoacetyl chloride (2 equivalents). The mixture is stirred for 45 minutes and added dropwise to a mixture of 80 ml of 2-propanol and 400 ml of diethyl ether. The resultant yellow solid is filtered and washed several times with diethyl ether and dried in vacuo to Give 1.25 G of the desired product.

$^1$H NMR(DMSO-$d_6$): δ 12.3(2,1H); 10.05(s,1H); 10.00(bs,1H); 9.6(s,1H); 9.1(s,1H); 8.3(s,1H); 4.3(s, 1H); 4.25(s,2H); 2.5–2.2 (m, 2H); 1.5(m, 1H).

MS (FAB): m/z 540 (M+H).

EXAMPLE 2-B

[4S- (4α, 12aα)]-9-[(Chloroacetyl)amino]-8-chloro-4-dimethylamino) -1,4,4a,5,5a,6,11,12a-octahydro-3,10,12,12a-tetrahydroxy-1,11-dioxo-2-naphthacenecarboxamide hydrochloride The titled compound is prepared by the above procedure using chloroacetyl chloride.

$^1$H NMR(DMSO-$d_6$): δ 12.3(s,1H); 9.85(s,1H); 9.55(s, 1H); 9.0(s,1H); 8.25(s,1H); 4.8(s,2H); 4.3(s,1H).

MS (FAB): m/z 540 (M+H).

EXAMPLE 3

[4S-(45, 12aα)] -8-Chloro-4-(dimethylamino)-9[[(dimethylamino)acetyl]amino]-1,4,4a,5,5a, 6,11,12a-octahydro-3,10,12,12a-tetrahydroxy-1,11-dioxo-2-naphthacenecarboxamide disulfate A well stirred solution, at 25° C., of 0.281 g of product from Example 1, 10 ml of DMPU, 3 ml of acetonitrile and 0.3 g of sodium carbonate is treated with 0.157 g of N,N-dimethylaminoacetyl chloride hydrochloride. After 30 minutes, the reaction is filtered and the filtrate is added dropwise to 300 ml of diethyl ether. Concentrated sulfuric acid is added dropwise and a yellow solid precipitates. The yellow solid is collected, washed well with diethyl ether, and dried in vacuo to give 0.21 g of the desired product.

MS (FAB): m/z 549 (M+H).

EXAMPLE 4

[4S-(4α, 12aα)]-9-[[(Butylamino)acetyl]amino]-8-chloro-4 -(dimethylamino) -1,4,4a,5,5a,6,11,12a-octahydro-3,10,12,12a-tetrahydroxy-1,11-dioxo-2-naphthacenecarboxamide dihydrochloride A mixture of 0.20 g of the product from Example 2, 0.5 g of n-butylamine and 3 ml of DMPU, under argon, is stirred at room temperature for 2 hours. The excess n-butylamine is removed in vacuo and the solids filtered. The filtrate is diluted with a small amount of methyl alcohol and the solution is added dropwise to a mixture of ml of 2-propanol and 120 ml of diethyl ether. The solution is treated dropwise with 1,0 M hydrogen chloride/diethyl ether solution to afford a yellow solid. The resulting solid is collected and dried in vacuo to give 0.175 g of the desired product.

MS(FAB): m/z 576(M+H).

Substantially following the method described in detail hereinabove in Example 4, the compounds of the invention listed below in Examples 5–11 are prepared.

EXAMPLE 5

[4S-(4α, 12aα)]-8-Chloro-4-(dimethylamino)- 1,4,4a,5,5a, 6,11,12a-octahydro-3,10,12,12a-tetrahydroxy-1,11-dioxo-9-[[(propylamino)acetyl]amino]-2 -naphthacenecarboxamide dihydrochloride $^1$H NMR(DMSO-$d_6$): δ 12.3(s,1H); 10.3(s,1H); 9.6(s, 1H); 9.05(s,1H); 8.3(s,1H); 4.35(s,1H); 4.0(s,2H); 0.9(t,3H).

MS(FAB): m/z 563 (M+H).

EXAMPLE 6

[4S-(4α, 12aα)]-8-Chloro-4-(dimethylamino)-1,4,4a,5,5a,6,11,12a-octahydro-3,10,12,12a-tetrahydroxy-1,11-dioxo-9-[[(pentylamino)acetyl]amino]-2 -naphthacenecarboxamide dihydrochloride $^1$H NMR(DMSO-$d_6$): δ 12.3(s,1H); 10.3(s,1H); 9.6(s, 1H); 9.05(s,1H); 8.3(s,1H); 4.35(s,1H); 4.05(s,2H); 2.8(s,6H); 0.9(m, 3H).

MS (FAB): m/z 592 (M+H).

EXAMPLE 7

[4S-(4α, 12aα)]-8-Chloro-4-(dimethylamino)-1,4,4a,5,5a,6,11,12a-octahydro-3,10,12,12a-tetrahydroxy-1,11-dioxo-9-[[(methylamino)acetyl]amino]-2-naphthacenecarboxamide dihydrochloride $^1$H NMR(DMSO-$d_6$): δ 12.3(s,1H); 10.3(s,1H); 9.55(s, 1H); 9.05(s,1H); 8.3(s,1H); 4.3(s,1H); 4.0(s,2H); 1.5(m, 1H) .

MS (FAB: m/z 535 (M+H).

EXAMPLE 8

[4S-(4α,12aα)]-8-Chloro-9-[[(cyclopropylmethylamino)-acetyl] amino]4-(dimethylamino)-1,4,4a,5,5a, 6,11,12a-octahydro-3,10,12,12a-tetrahydroxy-1,11-dioxo-2-naphthacenecarboxamide dihydrochloride $^1$H NMR(DMSO-$d_6$): δ 10.1(bs,1H); 8.9(bs,1H); 8.2(s, 1H); 2.6(s,6H); 2.3–2.0(m, 2H); 1.5(m, 1H); 0.65–0.40(m, 4H).

MS (FAB): m/z 575 (M+H).

EXAMPLE 9

[7S-(7α,10aα)]-N-[9-(Aminocarbonyl)-3-chloro-7-(dimethylamino)-5,5a,6,6a,7,10,10a,12-octahydro-1,8,10a, 11-tetrahydroxy -10,12-dioxo-2-naphthacenyl]-1 -pyrrolidineacetamide dihydrochloride $^1$H NMR(DMSO-d$_6$): δ 10.2(s,1H); 9.5(s,1H); 9.35(bs, 2H); 8.2(s,1H); 4.3(s,1H); 4.25(s,2H); 2.0–1.8(m, 4H); 1.5(m, 1H).
MS (FAB): m/z 575 (M+H).

EXAMPLE 10

7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-1-piperidineacetamide dihydrochloride $^1$H NMR(DMSO-d$_6$): δ 12.3(s,1H); 10.4(s,1H); 10.05(bs, 1H); 9.55(s,1H); 9.05(s,1H); 8.25(s,1H); 4.35(s,1H); 4.25(s,2H); 2.5–2.2(m, 2H); 1.9–1.3(m, 7H).
MS (FAB): m/z 589 (M+H).

EXAMPLE 11

[4S-(4α,12aα)]-8-Chloro-4,7-bis(dimethylamino)-1,4,4a,5,5a,6,11,12a-octahydro-3,10,12,12a-tetrahydroxy-1,11 -dioxo-2-naphthacenecarboxamide sulfate To a 0° C. solution of 0.090 g of [4S-(4α,12aα)]-8-Chloro-4,7-bis(dimethylamino)-1,4,4a,5-5a, 6,11,12a-octahydro-3,10,12,12a-tetrahydroxy-1,11-dioxo- 2-naphthacenecarboxamide, prepared by the procedure of U.S. patent application Ser. No. 214,992 filed 3/21/94, dissolved in 35 ml of 0.1N methanolic hydrogen chloride is added 0.2 ml of butyl nitrite. The reaction is stirred at room temperature for 1 hour, poured into 70 ml of diethyl ether and collected to give 0.070 g of the desired diazonium chloride intermediate.

A solution of 0.070 g of the above intermediate dissolved in 20 ml of methyl alcohol is heated at the reflux temperature for 45 minutes, poured into diethyl ether and collected to give 0.056 g of the desired product.
MS (FAB): m/z 491 (M$^+$).

EXAMPLE 12

[4S -(4α,12aα)]-9-[(2-Bromo-1-oxopropyl)amino]-8-chloro-4 -(dimethylamino)-1,4,4a,5,5a,6,11,12a, -octahydro-3,10,12,12a-tetrahydroxy-1,11-dioxo-2-naphthacenecarboxamide monosulfate To a room temperature solution of 9-amino-8-chloro-4-(dimethylamino)-1,4,4a,5,5a,6,11,12a-octahydro- 3,10, 12,12a-tetrahydroxy-1,11-dioxo-2-naphthacenecarboxamide sulfate in 2 ml of acetonitrile is added 6 ml of DMPU and 0.432 g of 2-bromopropionyl bromide. The reaction mixture is stirred at room temperature for 40 minutes. Two ml of methyl alcohol is added and the reaction is poured into a mixture of isopropanol/diethyl ether. The resulting solid is collected, washed with diethyl ether and dried to give o.54 g of the desired product, which is used without further purification.

$^1$H NMR(DMSO-d$_6$): δ 12.3(s,1H); 10.0(s,1H); 9.55(s, 1H); 9.05(s,1H); 8.3(s,1H); 5.1(m, 1H); 4.3(s,1H); 2.75(s,6H); m2.2–2.45(m, 2H); 1.5(m, 1H); 1.75(d, 3H).
MS (FAB): m/z 600 (M+H).
Exact Mass (M+H): 598. 0587; Δ=+0.5 mmµ.

EXAMPLE 13

7S-(7α,10aα)]-N-[9-(Aminocarbonyl)-3-chloro-7-(dimethylamino)-5,5a,6,6a,7,10,10a,12-octahydro-1,8,10a,11 -tetrahydroxy-10,12-dioxo-2-naphthacenyl]-α-methyl-1-pyrrolidineacetamide dihydrochloride A room temperature mixture of 0.15 g of product from Example 12, 0.45 g of pyrrolidine and 5 ml of DMPU is stirred for 24 hours. The excess pyrrolidine is removed and the residue is added to a mixture of isopropanol and diethyl ether. 1.0 M hydrochloric acid/diethyl ether is added until a yellow precipitate is observed. The solid is collected, washed and dried. The crude product is dissolved in water, the pH is adjusted to 3–4 using ammonium hydroxide, and extracted with chloroform. This organic extract is discarded. The pH of the mixture is adjusted to between 5–6, extracted numerous times with chloroform, the extracts are combined, washed, dried and concentrated. The residue is redissolved in a minimum amount of chloroform, and 30 ml of 1.0 M hydrochloric acid/diethyl ether is added. The resulting precipitate is collected, washed and dried.

$^1$H NMR(DMSO-d$_6$): δ 12.3(s,1H); 10.75(bs,1H); 10.45(s,1H); 9.6(s,1H); 9.05(s,1H); 8.2(s,1H); 4.4(m, 1H); 4.35(s,1H); 2.85 (bs, 6H); 3.0–2.25 (m, 2H); 2.15–1.8 (m, 4H); 1.55 ( d, 3H); 1.5 (m, 1H).
MS (FAB): m/z 589 (M+H).
Exact Mass: 589.2073, Δ=–0.8 mmµ.

EXAMPLE 14

7S- (7α, 10aα)]-N-[9- (Aminocarbonyl)-3-chloro-7-(dimethylamino)-5,5a,6,6a,7,10,10a,12-octahydro-1,8,10a,11 -tetrahydroxy-10,12-dioxo-2-naphthacenyl]-α-methyl-1 -piperidineacetamide dihydrochloride The title compound is prepared by the procedure of Example 13 using 0.15 g of product from Example 12, 0.6 g of piperidine and 5 ml of DMPU to give, after purification at pH 5–6, 0.070 g of the desired product.

$^1$H NMR(DMSO-d$_6$): δ 12.3(s,1H); 10.5(s,1H); 10.35(bs, 1H); 9.53(s,1H); 9.05(s,1H); 8.2(s,1H); 4.4(m, 1H); 4..3s,1H); 2.9 (bs, 6H); 1.55 ( d, 3H); 1.45 (m, 1H) .
MS(FAB): m/z 603(M+H).
Exact Mass (M+H)=603.2219, Δ=+0.3 mmµ.

EXAMPLE 15

[4S- (4α,12aα)]-8-Chloro-4- (dimethylamino)-1,4,4a,5,5a,6,11,12a,-octahydro-3,10,12,12a-tetrahydroxy-1,11-dioxo-9-[[[(1-methylethyl)amino]acetyl]amino]-2-naphthacenecarboxamide dihydrochloride The title compound is prepared by the procedure of Example 13 using 0.15 g of product Example 2-B, 0.50 g of isopropyl amine, and 5 ml of DMPU to give, after purification at pH 5–7, 0.08 g of the desired product.

¹H NMR(DMSO-d₆): δ 12.3(s,1H); 10.25(s,1H); 9.55(s, 1H); 9.05(s,1H); 8.28(s,1H); 4.3(s,1H); 4.1(bs,2H); 2.85(s,6H); 2.5–2.2 (m, 2H); 1.5(m, 1H); 1.25(d, 6H).

MS (FAB): m/z 563 (M+H).

Exact Mass (M+H)=563.1903, Δ=+0.6 mmµ.

EXAMPLE 16

[4S-(4α,12aα)]-8
-Chloro-4-(dimethylamino)-9-[[(2-(dimethylamino)
-1-oxopropyl]amino]-1,4,4a,5,5a,6,11,12a-octahydro-
3,10,12,12a-tetrahydroxy-1,11-dioxo-9-[[[(1
-methylethyl)amino]acetyl]amino]-
2-naphthacenecarboxamide dihydrochloride The title compound is prepared by the procedure of Example 13 using 0.15 g of product from Example 12, 1 ml of 40% dimethylamine and 5 ml of DMPU to give after purification 0.11 g of the desired product.

¹H NMR(DMSO-d₆): δ 12.3(s,1H); 10.4(s,1H); 9.55(s, 1H); 9.05(s,1H); 8.2(s,1H); 4.35(m, 1H); 4.3(s,1H); 2.8(s,6H); 2.5(s,6H); 2.5–2.2(m, 2H); 1.55(d,3H).

MS(FAB): m/z 563(M+H)

Exact Mass (M+H)=563.1920, Δ=−1.1 mmµ.

EXAMPLE 17

[4S-(4α,12aα)]-9-[(2-Bromo-1-oxobutyl)amino]-8-
chloro-4-(dimethylamino)-
1,4,4a,5,5a,6,11,12a.-octahydro-
3,10,12,12a-tetrahydroxy-1,11-dioxo-2-
naphthacenecarboxamide monosulfate The title compound is prepared by the procedure of Example 12 using 0.673 g of 9-amino-8-chloro-4-(dimethylamino)- 1,4,4a,5,5a,6,11,12a-octahydro-3,10,12,12a-tetrahydroxy- 1,11-dioxo-2-naphthacenecarboxamide sulfate, 0.552 g of (±) 2-bromobutylbromide, 12 ml of DMPU, and 5 ml of acetonitrile to 0.75 g of the desired product.

¹H NMR(DMSO-d₆): δ 12.3 (s,1H); 10.0(s,1H); 9.55(s, 1H); 9.05(s,1H); 8. 3(s,1H); 4.9(m, 1H); 4.3(s,1H); 2.75(s,6H); 2.5–2.2 (m, 2H); 1.85 (m, 2H); 1.5 (m, 1H); 0.98 ( t, 3H).

MS ( FAB ): m/z 6 14 (M+H).

Exact Mass (M+H)=612.0745, Δ=+0.3 mmµ.

EXAMPLE 18

[4S-(4α,12aα)]-8-Chloro-4-(dimethylamino)-9-
[[(2-(dimethylamino)-
1-oxobutyl]amino]-1,4,4a,5,5a,
6,11,12a-tetrahydroxy-1,11-dioxo-9-[[[(1
-methylethyl)amino]acetyl]amino]-
2-naphthacenecarboxamide dihydrochloride The title compound is prepared by the procedure of Example 13 using 0.15 g of product from Example 17, 1.25 ml of 40% dimethylamine and 4 ml of DMPU, for 1 hour, to give 0.12 g of the desired product.

¹H NMR(DMSO-d₆): δ 12.3 (s,1H); 10.5(s,1H); 9.55(s, 1H); 9.05(s,1H); 8.6(bs,1H); 8.2(s,1H); 4.3(s,1H); 4.2(m, 1H); 2.8(s,6H); 2.5(s,6H); 2.0–1.8(m, 2H); 1.5(m, 1H); 0.98(t,3H).

MS (FAB): m/z 577 (M+H).

Exact Mass (M+H)=577.2075, Δ=−1.0 mmµ.

EXAMPLE 19

7S-(7α, 10aα)]-N- 8
9-(Aminocarbonyl)-3-chloro-7-(dimethylamino)-
5,5a,6,6a,7,10,10a,12-octahydro-1,8,10a,11
-tetrahydroxy-10,12-dioxo-2-naphthacenyl]-α-ethyl-1
-piperidineacetamide dihydrochloride The title compound is prepared by the procedure of Example 13 using 0.15 g of product from Example 17, 0.45 g of pyrrolidine and 4 ml of DMPU to give 0.05 g of the desired product.

¹H NMR(DMSO-d₆): δ 12.3 (s, 1H); 10.7 (BS,1H); 10.05(s,1H); 9.55(s,1H); 9.05(s,1H); 8.2(s,1H); 4.3(s, 1H); 4.25(m, 1H); 2.85 (bs, 6H); 2.5 (s, 6H); 2.5–2.2(m, 2H); 2.15–1.75(m, 6H); 1.5(m, 1H); 0.98(t, 3H).

MS(FAB): m/z 603 (M+H).

Exact Mass (M+H)=603.225, Δ=−0.3 mmµ.

BIOLOGICAL ACTIVITY

The antiproliferative activity of the compounds of Formula I in an Adult Bovine Aortic Endothelial (ABAE) cell line and in Human Tumor cell lines is evaluated in three similar assays that measure growth inhibition. The assays are identified as follows:

PROTOCOL 1

PROTOCOL 2 and

PROTOCOL 3.

PROTOCOL 1,2,and 3 are described in greater detail hereinbelow. In general, according to PROTOCOLS 1 and 2, the target ABAE and/or Human Tumor cells are exposed to the compounds of Formula I for 48 hours. PROTOCOL 3 exposes ABAE cells to the compounds for 4 days. A detailed description of the protocols is as follows:

Biological Protocols

PROTOCOL 1

Antiproliferative Activity in Human Tumor and Adult Bovine

Aortic Endothelial Cell Lines (ABAE)

The antiproliferative activity of the compounds of Formula I of the present invention is evaluated in a panel comprised of human tumor cell lines and an adult bovine aortic endothelial cell line (ABAE). The human tumor cell lines are from 1) Ovarian tumors:

HTB161, A2780S and A2789/DDP; and

2) Colon tumors:

MIP, CaCo2, and SW620.

All cell lines are maintained in log phase in RPMI 1640 media, supplemented with 5% fetal calf serum, penicillin/ streptomycin and 2 mM L-glutamine. Cultures are renewed after 20 passages with cells from a fresh stock of batch-frozen early passage cells. Cell lines are routinely checked for mycoplasma contamination (Genprobe). In a laminar flow hood, cells (1–5×10⁴) are plated into 96-well microtiter plates in a volume of 0.1 ml/well with a bulk microtiter dispenser (Denley). Twenty-four hours after cell plating, test compounds are added in duplicate over a 5-log concentration range, starting with 100 microgram/ml, in a diluent such that the final concentration of dimethylsulfoxide in cell culture medium does not exceed 1% (v/v). At this concentration, dimethylsulfoxide has no effect on cell growth. Compounds are added using a Tomtec dispenser which simultaneously dispenses from one 96-well plate, containing the drug dilutions, to the plates containing the cells. After two days of continuous drug exposure, 50% cold trichloroacetic acid (TCA) is added to 10% final concentration to fix the cells, and after 60 minutes at 4° C., the TCA is aspirated and the plates are washed 5 times with deionized water using a microtiter plate washer. The number of cells on the plate are quantitated using a protein dye-binding assay (Monks et al., 1991). A 0.4% solution of the dye, sulforhodamine B, in glacial acetic acid is added to the plates, and the plates are washed 5 times with 1% glacial acetic acid using the automatic plate washed. The bound stain is solubilized with 0.1 ml of 10 mM Tris base. The optical densities are read from an automatic spectrophotometric plate reader (Dynatech) directly to a main frame computer (VAX 8600).

Positive controls, that include standard chemotherapeutic drugs (i.e., Adriamycin, Cisplatin, etc.), are included in every experiment.

Background optical density measurements (complete media–cells, and complete media+drug–cells) are automatically subtracted from the appropriate control and test wells. Mean values and standard errors are determined from duplicate wells. A measure is also made of the optical density at time when the drugs are added. The number of cells after treatment (P), as % of control, is calculated for every concentration of drug, as follows:

$$P = \frac{(T - C_o)}{(C - C_o)} \times 100$$

wherein:

T is optical density measurement for treated cells after 48 hours;

C is optical density measurement for untreated cells after 48 hours;

$C_o$ is optical density measurement for cells at the time of drug addition.

$IC_{50}$ of growth inhibition is calculated from the sets of P values using the RS-1 data package (BBN Software).

PROTOCOL 2
Antiproliferative Activity in Human Tumor and Adult Bovine Aortic Endothelial Cell Lines (ABAE)

The antiproliferative activity of the compounds of Formula I is evaluated in a panel comprised of human tumor cell lines and an adult bovine aortic cell line (ABAE) as listed in PROTOCOL 1. This assay is a modification of PROTOCOL 1. The modifications include:

1) each concentration for each compound is tested in a single well;

2) compounds are tested at 20, 4, 0.8, 0.16 microgram/ml and additionally in some experiments at 100 and 0.32 microgram/ml;

3) samples are pipetted into a 96-well plate for each of the cell lines by a Beckman Biomek 1000 SL robot;

4) after fixing with TCA each well is washed with 0.35 ml distilled water twice, not five times;

5) after staining with sulforhodamine B each well is washed 3 times, not five times;

6) the growth inhibition (I) as % of control, is calculated using the RS-1 data package (BBN Software), for every concentration of drug, as follows:

$$I = \frac{[1 - (T)]}{(C)} \times 100$$

wherein:

T is optical density measurement for treated cells after 48 hours;

C is optical density measurement for untreated cells after 48 hours;

7) $IC_{50}$ of growth inhibition is determined graphically from dose response curves, as is known in the art.

PROTOCOL 3
Antiproliferative Activity in Adult Bovine Aortic Endothelial (ABAE) Cell Line ABAE cells are grown in DMEMmedia (Mediatech, Washington, D.C.) supplemented with 10% calf serum (Hyclone). ABAE cells are plated in 24-well dishes at 8,000 cells/well, followed by the addition of increasing concentrations of 7-(hydrogen or di($C_1$-$C_4$)alkylamino)-8 -halogen-9-(substituted)-6-demethyl-6-deoxytetracycline. After four days, the cells are detached and counted. In the control wells, cells did not reach confluency during experimental time. The growth inhibition (I) as % of control is calculated as follows:

$$I = \frac{[1 - (N_t - N_o)]}{(N_c - N_o)} \times 100$$

wherein:

$N_c$ is the number of cells in untreated wells;

$N_t$ is the number of cells in treated wells;

$N_o$ is the number of plated cells.

$IC_{50}$ of growth inhibition is determined from the sets of I values plotted by Kaleidograph software (Abelbeck Software).

Table 1 presents the results depicting the antiproliferative activity of the compounds of Formula I against an Adult Bovine Aortic Endothelial cell line (ABAE), as evaluated by PROTOCOL 1 and 2. The results are presented in terms of $IC_{50}$ and are as follows.

TABLE 1

Antiproliferative Activity in Adult Bovine Aortic Endothelial (ABAE) Cell Line

| COMPOUND OF EXAMPLE NO. | $IC_{50}$ PROTOCOL 1 | PROTOCOL 2 |
| --- | --- | --- |
| 14 | ND | <0.8 |
| 10 | 0.7 | ND |
| 6 | 0.6 | ND |
| 9 | 2.5 | ND |
| 3 | 2.2 | ND |
| 5 | 2.0 | ND |
| 4 | 2.3 | ND |
| 8 | 2.0 | ND |
| 11 | 3.0 | ND |
| 13 | ND | 3.0 |
| 15 | ND | <1 |
| 19 | ND | 4.0 |
| 16 | ND | 3.0 |
| 18 | ND | 16 |
| 7 | 3.3 | ND |
| Prior Art Compound Minocycline | 6.8 | ≧20 |

ND = Not Determined

In addition FIG. 1, presents the dose response curve for the compound of Example 10 for the above ABAE cell line obtained by using PROTOCOL 3.

As can be seen from Table 1, the compounds with product of Formula I exhibit increased activity in inhibiting proliferation of ABAE cells as compared to the prior art compound, Minocycline. Also as can be seen from FIG. 1, the difference between the prior art compound Minocycline and the compound of Example 10 is more significant in a 4 day assay (PROTOCOL 3). It appears, that prior art compound Minocycline is loosing its activity upon incubation with cells, while the compound of Example 10 retains its activity. Minocycline inhibits 50% of cell growth at approximately 50 µg/ml, while the compound of Example 10 inhibits 50% of cell growth at approximately 0.4 µg/ml.

Table 2 presents the results depicting the antiproliferative activity of the compounds according to Formula I against a panel of Human Tumor Cell lines as evaluated by PROTOCOL 1 and PROTOCOL 2. The results are presented in terms of $IC_{50}$ values against each cell line and average $IC_{50}$ and are as follows.

TABLE 2

Antiproliferative Activity in Human Tumor Cell Lines

| COMPOUND FROM EXAMPLE NO. | OVARIAN TUMOR CELL LINES | | | COLON TUMOR CELL LINES | | | AVERAGE $IC_{50}$ FOR TUMOR CELL LINES |
|---|---|---|---|---|---|---|---|
| | A2780S $IC_{50}$ μg/ml | A2780/DDP $IC_{50}$ μg/ml | MIP $IC_{50}$ μg/ml | CACO2 $IC_{50}$ μg/ml | HTB 161 $IC_{50}$ μg/ml | SW620 $IC_{50}$ μg/ml | |
| 14 | <0.16 | <0.16 | <0.16 | 0.7 | <0.16 | <0.16 | ND |
| 10 | 0.5 | 0.6 | 0.7 | 0.65 | 0.6 | 0.6 | 0.6 |
| 6 | 0.5 | 0.7 | 1.5 | 0.7 | 0.5 | 0.8 | 0.8 |
| 13 | 1.0 | 1.0 | 1.0 | 3.0 | 1.0 | 1.0 | 1.3 |
| 9 | 1.3 | 1.0 | 0.8 | 1.7 | 1.9 | 2.0 | 1.45 |
| 16 | 1.0 | 1.0 | 1.0 | 4.0 | 1.0 | 1.0 | 1.5 |
| 3 | 1.8 | 2.5 | 2.2 | 1.65 | 1.0 | 2.3 | 1.9 |
| Prior Art Compound Minocycline | 6.1 | 6.1 | 6.1 | 9.0 | 5.8 | 6.5 | 6.6 |
| 19 | 1.0 | 1.0 | 3.0 | 4.0 | 2.0 | 3.0 | 2.3 |
| 8 | 2.2 | 2.5 | 3.8 | 2.8 | 1.0 | 2.4 | 2.45 |
| 4 | 2.5 | 2.8 | 3.1 | 2.5 | 1.2 | 2.8 | 2.5 |
| 11 | 1.6 | 3.85 | 2.6 | 3.6 | 0.7 | 4.5 | 2.8 |
| 16 | 3.0 | 3.0 | 3.0 | 8.0 | 3.0 | 3.0 | 3.8 |
| 5 | 3.0 | 3.0 | 10.0 | 4.0 | 4.0 | 3.5 | 4.6 |
| 7 | 4.6 | 3.8 | 8.5 | 3.8 | 1.3 | 4.0 | 4.3 |
| 18 | ND | 3.0 | 4.0 | 11.0 | 3.0 | 3.0 | 4.8 |
| Prior Art Compound Minocycline | 6.1 | 6.1 | 6.1 | 9.0 | 5.8 | 6.5 | 6.6 |

ND = Not Determined

Figure 2:
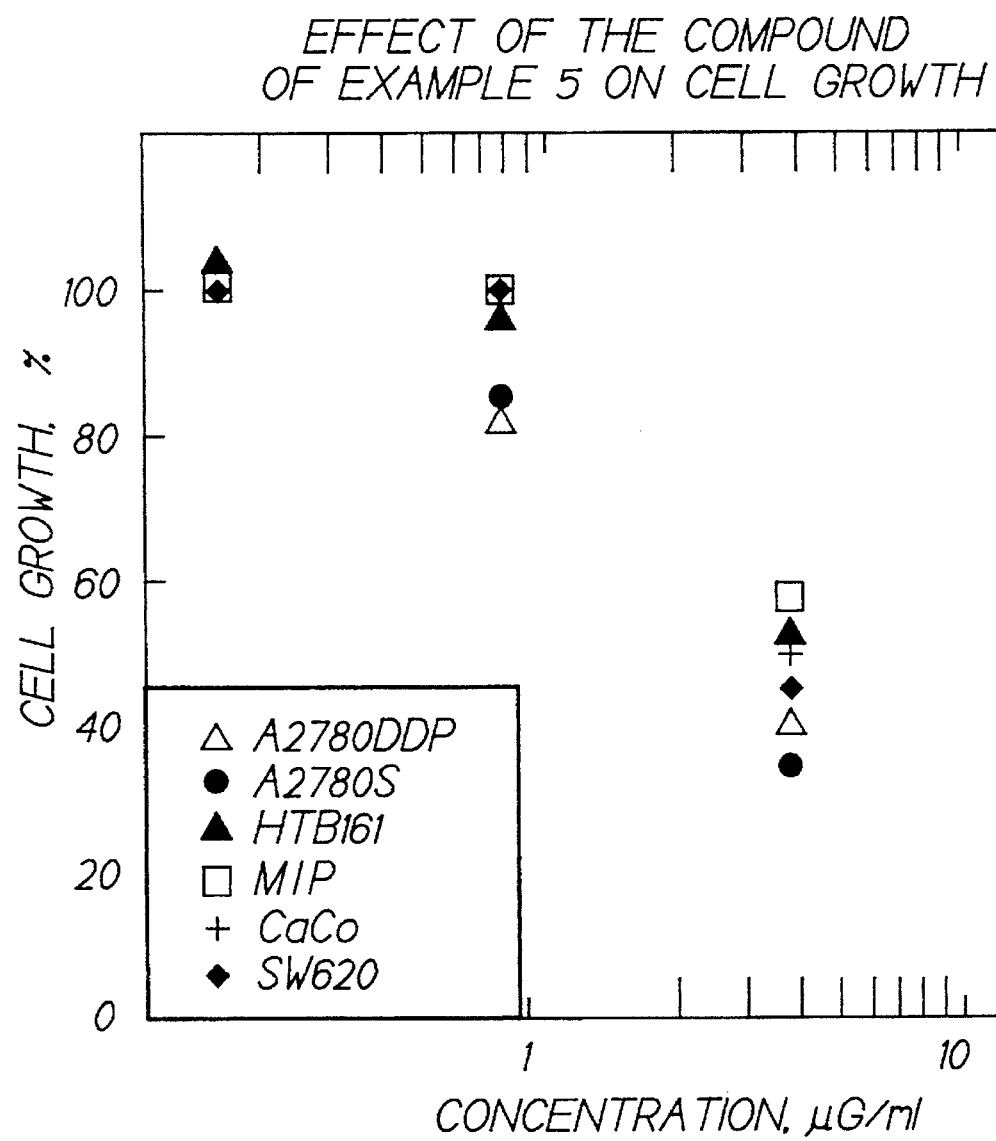
FIG. 2 depicts the effects of the compound of Example 5 on the cell growth of 6 Human Tumor cell lines.

FIG. 2 shows graphically the dose response curve for a compound of Example 5 against the 6 tested Human Tumor Cell lines.

As can be seen from Table 2, the compounds of Formula I exhibit increased activity in inhibiting the proliferation of tumor cell lines as compared to the prior art compound Minocycline. Also, as can be seen from FIG. 2, even at the highest concentrations of compound of Example 5 there is no 100% inhibition of cell growth. This result means that even at the highest concentration of compound of Example 5 the cells continue to grow. Dead floating cells were not observed even at the highest concentration of compound of Example 5 or other compounds of Formula I. Taken together, these data indicate that compounds of Formula I are inhibitors of cell growth, or cytostatic compounds, rather than cytotoxic compounds to the cells.

The data from both Tables 1 and 2 demonstrate that the compounds of Formula I are more potent in inhibiting endothelial and tumor cells, than the Minocycline compound utilized by Breem et al and Teicher et al. This is of particular importance as a more potent compound can inhibit tumor cells, endothelial cells, and vascular growth more effectively, thus permitting the use of smaller doses. Also, such compounds will have a greater efficacy for keeping tumor growth in check after chemotherapy or radiation therapy. This translates directly into a real benefit of requiring fewer repetitions of chemotherapy and radiation therapy to eradicate a tumor. Also, such compound permit intervals between radiation or chemotherapy to be longer without significant tumor regrowth.

We claim:

1. A method for inhibiting angiogenesis and endothelial cell proliferation which comprises administering an effective inhibitory amount of a compound of formula I:

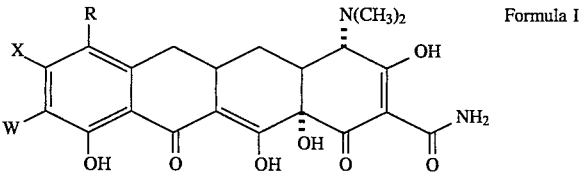

Formula I wherein:

R is hydrogen or a di($C_1$–$C_4$)alkylamino;

X is halogen selected from bromine, chlorine, fluorine and iodine;

W is hydrogen or a moiety of the formula:

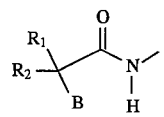

wherein:

$R_1$ and $R_2$ are hydrogen or ($C_1$–$C_3$)alkyl;

B is ($R_3$)$_2$N—; $R_3$NH— or ($C_2$–$C_5$)azacycloalkane wherein $R_3$ is ($C_1$–$C_7$)alkyl, or ($C_3$–$C_5$)cycloalkylmethyl; or a pharmaceutically acceptable salt thereof;

alone or in combination with a therapeutic agent used in the treatment of an angiogenic disorder;

to a warm blooded animal having a disorder characterized by the undesired proliferation of endothelial cells.

2. The method according to claim 1, wherein the compound of formula I is selected from the group consisting of

[4S-(4α,12aα)]-8-chloro-4-(dimethylamino)-9-[[(dimethylamino)acetyl]amino]-1,4,4a,5,5a,6,11,12a-octahydro- 3,10,12,12a-tetrahydroxy-1,11-dioxo-2-naphthacenecarboxamide disulfate;

4S- (4α, 12aα)]-9-[[(butylamino)acetyl]amino ]-8-chloro-4-(dimethylamino)- 1,4,4a, 5,5a, 6,11,12a-octahydro-3,10,12,12a-tetrahydroxy- 1,11-dioxo-2-naphthacenecarboxamide dihydrochloride;

[4S-(4α,12aα)]-8-chloro-4-(dimethylamino)-1,4,4a,5,5a, 6,- 11,12a-octahydro-3,10,12,12a-tetrahydroxy-1,11-dioxo-9-[[(propylamino)acetyl]amino]-2-naphthacenecarboxamide dihydrochloride;

[4S- (4α,12aα)]-8-chloro-4-(dimethyamino) -1,4,4a,5,5a, 6,- 11,12a-octahydro-3,10,12,12a-tetrahydroxy-1,11-dioxo-9[[(pentylamino)acetyl]amino]-2-naphthacenecarboxamide dihydrochloride;

[4S-(4α,12aα)]-8-chloro-4-(dimethylamino)-1,4,4a,5,-5a,6,11,12a-octahydro-3,10,12,12a-tetrahydroxy-1,11-dioxo- 9-[[(methylamino)acetyl]amino]-2-naphthacenecarboxamide dihydrochloride;

[4S-(4α,12aα)]-8-chloro-9-[[(cyclopropylmethylamino)acetyl ]amino]4-(dimethylamino)-1,4,4a,5,5a,6,-11,12a-octahydro- 3,10,12,12a-tetrahydroxy-1,11-dioxo-2-naphthacenecarboxamide dihydrochloride;

[7S-(7α,10aα)]-N-[9-(aminocarbonyl)-3-chloro-7-(dimethylamino)- 5,5a,6,6a,7,10,10a,12-octahydro-1,8,10a,11-tetrahydroxy- 10,12-dioxo-2-naphthacenyl]-1-pyrrolidineacetamide dihydrochloride;

7S-(7α, 10aα)]-N-[9-(aminocarbonyl)-3-chloro-7-(dimethylamino)- 5,5a,6,6a,7,10,10a,12-octahydro-1,8,10a,11 -tetrahydroxy-10,12-dioxo-2-naphthacenyl]-1-piperidineacetamide dihydrochloride;

[4S- (4α,12aα)]-8-chloro-4,7-bis(dimethylamino)- 1,4,4a,5,5a,6,11,12a-octahydro-3,10,12,12a-tetrahydroxy-1,11 -dioxo-2-naphthacenecarboxamide sulfate;

7S- (7α,10aα)]-N-[9-(aminocarbonyl)-3-chloro-7-(dimethylamino)- 5,5a,6,6a,7,10,10a,12-octahydro-1,8,10a,11 -tetrahydroxy-10,12-dioxo-2-naphthacenyl]-5-methyl-1-pyrrolidineacetamide dihydrochloride;

7S- (7α,10aα)]-N-[9-(aminocarbonyl)-3-chloro-7-(dimethylamino)- 5,5a,6,6a,7,10,10a,12-octahydro-1,8,10a,11 -tetrahydroxy-10,12-dioxo-2-naphthacenyl]-α-methyl -1-piperidineacetamide dihydrochloride;

[4S-(4α,12aα)]-8-chloro-4-(dimethylamino)-1,4,4a,5, 5a,6, -11,12a, -octahydro-3,10,12,12a-tetrahydroxy-1,11-dioxo-9-[[[(1-methylethyl)amino]acetyl]amino]-2-naphthacenecarboxamide dihydrochloride;

[4S-(4α,12aα)]-8-chloro-4-(dimethylamino)-9-[[(2-(dimethylamino)- 1-oxopropyl]amino]-1,4,4a,5,5a,6,11,12a-octahydro- 3,10,12,12a-tetrahydroxy-1,11-dioxo-9-[[[(1 -methylethyl)amino]acetyl]amino]-2-naphthacenecarboxamide dihydrochloride,

[4S-(4α,12aα)]-8-chloro-4-(dimethylamino)-9-[[(2-(dimethylamino)- 1-oxobutyl]amino]-1,4,4a,5,5a,6,11,12a-octahydro- 3,10,12,12a-tetrahydroxy-1,11-dioxo-9-[[ [(1-methylethyl)amino]acetyl]amino]-2-naphthacenecarboxamide dihydrochloride; and 7S- (7α,10aα)]-N-[9-(aminocarbonyl)-3-chloro-7-(dimethylamino)- 5,5a,6,6a,7,10,10a,12-octahydro-1,8,10a, 11 -tetrahydroxy-10,12 -dioxo-2-naphthacenyl]-α-ethyl-1-piperidineacetamide dihydrochloride.

3. The method according to claim 11 wherein the compound of formula I is selected from the group consisting of

[4S-(4α,12aα)]-8-chloro-4-(dimethylamino)-1,4,4a,5,5a, 6,- 11,12a-octahydro-3,10,12,12a-tetrahydroxy-1,11-dioxo-9-[[(pentylamino)acetyl]amino]-2-naphthacenecarboxamide dihydrochloride;

7S- (7α,10aα)]-N-[9-(aminocarbonyl)-3-chloro-7-(dimethylamino)- 5,5a,6,6a,7,10,10a,12-octahydro-1,8,10a, 11 -tetrahydroxy-10,12-dioxo-2-naphthacenyl]-1-piperidineacetamide dihydrochloride; and 7S-(7α,10aα)]-N-[9-(aminocarbonyl)-3-chloro-7-(dimethylamino)- 5,5a,6,6a,7,10,10a,12-octahydro-1,8,10a, 11 -tetrahydroxy-10,12-dioxo-2-naphthacenyl]-α-methyl-1-piperidineacetamide dihydrochloride.

4. The method of claim 1, wherein the effective amount of the compound of Formula I is from about 0.10 to 30.0 mf per kg of body weight.

5. The method of claim 4, wherein the amount is from about 1.0 to 10.0 mg per kg of body weight.

6. The method of claim 1, wherein the compound of formula I is embedded in a biocompatible controlled release matrix.

* * * * *